United States Patent [19]

Lerch et al.

[11] Patent Number: 4,831,028
[45] Date of Patent: * May 16, 1989

[54] NOVEL BENZOTHIAZINONE DERIVATIVES, PROCESSES FOR THEIR PREPARATION, MEDICAMENTS CONTAINING THEM AND THEIR USE

[75] Inventors: Ulrich Lerch, Hofheim am Taunus; Rainer Henning, Hattersheim am Main, both of Fed. Rep. of Germany

[73] Assignee: Hoechst Aktiengesellschaft, Frankfurt am Main, Fed. Rep. of Germany

[*] Notice: The portion of the term of this patent subsequent to Jun. 17, 2003 has been disclaimed.

[21] Appl. No.: 42,867

[22] Filed: Apr. 24, 1987

[30] Foreign Application Priority Data

Apr. 28, 1986 [DE] Fed. Rep. of Germany ....... 3614355

[51] Int. Cl.$^4$ .................... A61K 31/54; C07D 279/10
[52] U.S. Cl. .................... 514/224.2; 544/52
[58] Field of Search ........................ 544/52; 514/225

[56] References Cited

U.S. PATENT DOCUMENTS 4,584,300 4/1986 Iwao et al. ..................... 514/225
4,595,685 6/1986 Henning et al. ................. 544/52

FOREIGN PATENT DOCUMENTS 0116368 8/1984 European Pat. Off. .
0146893 7/1985 European Pat. Off. .

*Primary Examiner*—Mary C. Lee
*Assistant Examiner*—Zinna Northington
*Attorney, Agent, or Firm*—Finnegan, Henderson, Farabow, Garrett, Dunner

[57] ABSTRACT

Benzothiazinone derivatives I

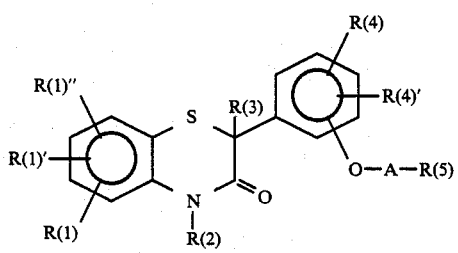

with $R^1$ and $R^4$ being H, alkyl, alkoxy, Hal, $CF_3$, $NO_2$, OH, acetamido or amino, $R^2$ being H, (cyclo)alk(en)yl, cycloalkylakyl, phenyl or phenylalkyl, A being $(CH_2)_mO(CH_2)_n$, $(CH_2)_p—CH(OH)—CH_2)_q$, $(CH_2)_p—CH(OCH_3)—(CH_2)_q$, or $(CH_2)_rOCH_2—CO—$ and $(CH_2)_s—CO—$, $R^5$ being NR(6)R(7) or certain cyclic amines, show a calcium-antagonistic action.

They are obtained, inter alia, from II

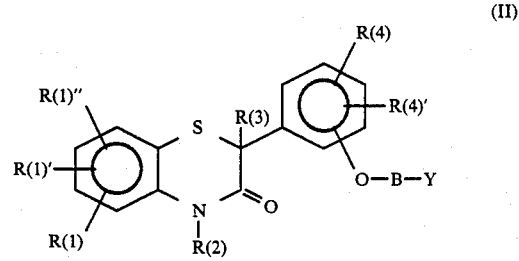

by reaction with III

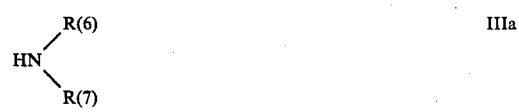

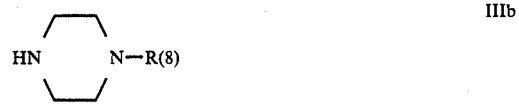

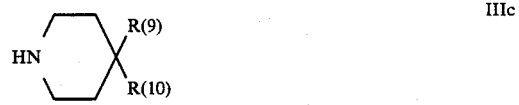

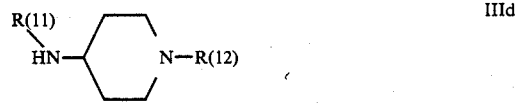

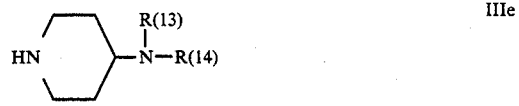

A and B are same or different and are lower alkylene having 1 to 6 carbon atoms; and n is 3 to 4.

5 Claims, No Drawings

NOVEL BENZOTHIAZINONE DERIVATIVES, PROCESSES FOR THEIR PREPARATION, MEDICAMENTS CONTAINING THEM AND THEIR USE

It is known that compounds which hinder the influx of calcium ions into cells can be used as therapeutic agents for the treatment of various diseases, in particular of the cardiovascular system, in man and other warm-blooded animals.

Benzothiazinone derivatives having a calcium-antagonistic action are described in U.S. Pat. No. 4,584,300; the compounds listed therein are unsubstituted in the 2-position of the heterocyclic ring.

Benzothiazinone derivatives having a calcium-antagonistic action are also to be found in U.S. Pat. No. 4,595,685. In the latter, compounds are described which carry a basic ether grouping on the 2-phenyl radical, the basic nitrogen being linked to the ether oxygen via a straight-chain or branched alkyl chain.

It has now been found, surprisingly, that compounds with a modified side chain on the 2-phenyl radical show superior calcium-antagonistic properties.

The invention therefore relates to novel benzothiazinone derivatives of the formula I, which have a calcium-antagonistic action:

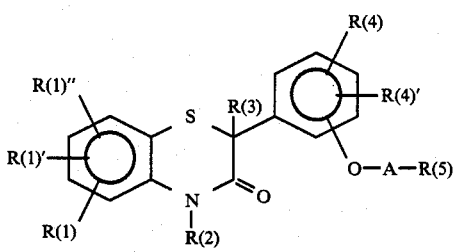

in which

R(1), R(1)' and R(1)" are identical or different and independently of one another are hydrogen, $(C_1-C_4)$-alkyl, $(C_1-C_3)$-alkoxy, F, Cl, Br, $CF_3$, nitro, hydroxyl, acetamido or amino, R(2) is hydrogen, straight-chain or branched $(C_1-C_{10})$-alkyl, straight-chain or branched $(C_3-C_{10})$-alkenyl or phenyl-$(C_1-C_4)$-alkyl, the phenyl ring being unsubstituted or substituted by one, two or three substituents from the group comprising $(C_1-C_4)$-alkyl, $(C_1-C_3)$-alkoxy, F, Cl, $CF_3$, $(C_1-C_2)$-alkylenedioxy or nitro, R(3) is hydrogen, straight-chain or branched $(C_1-C_{15})$-alkyl, straight-chain or branched $(C_3-C_{15})$-alkenyl, $(C_4-C_8)$-cycloalkyl, $(C_4-C_8)$-cycloalkyl-$(C_1-C_4)$-alkyl, phenyl, or phenyl-$(C_1-C_4)$-alkyl, the phenyl radical being unsubstituted or substituted by one, two or three substituents from the group comprising $(C_1-C_4)$-alkyl, $(C_1-C_3)$-alkoxy, F, Cl, $CF_3$, $(C_1-C_2)$-alkylenedioxy or nitro, R(4) and R(4)' are identical or different and independently of one another are hydrogen, $(C_1-C_4)$-alkyl, $(C_1-C_3)$-alkoxy, F, Cl, $CF_3$, nitro, hydroxyl, acetamido or amino, A is the group $-(CH_2)_m-O-(CH_2)_n-$, m and n each being 2 or 3, or one of the groups $-(CH_2)_p-CH(OH)-(CH_2)_q-$ and $-(CH_2)_p-CH(OCH_3)-(CH_2)_q-$, p and q) each being 1, 2 or 3, or the group $-(CH_2)_r-O-CH_2CO-$, r being 2 or 3, or the group $-(CH_2)_s-CO-$, s being 1, 2, 3 or 4, R(5) is one of the following groups

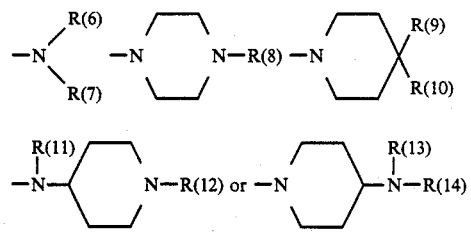

in which

R(6) and R(7) are identical or different and independently of one another are hydrogen, $(C_1-C_{10})$-alkyl, $(C_4-C_8)$-cycloalkyl, $(C_4-C_8)$-cycloalkyl-$(C-C_4)$-alkyl, pyridyl-$(C_1-C_4)$-alkyl, phenyl-$(C_1-C_6)$-alkyl, benzhydryl or benzhydryl-$(C_1-C_4)$-alkyl, the phenyl radicals in each case being unsubstituted or substituted by one, two or three radicals from the group comprising $(C_1-C_4)$-alkyl, $(C_1-C_4)$-alkoxy, $(C_1-C_2)$-alkylenedioxy, F, Cl, Br, $CF_3$ or hydroxyl, R(8) is hydrogen, straight-chain or branched $(C_1-C_{10})$-alkyl, $(C_1-C_8)$-alkanoyl, pyridyl, pyrimidinyl, phenyl, phenyl-$(C_1-C_4)$-alkyl, phenyl-$(C_3-C_5)$-alkenyl, benzyhydryl or benzhydryl-$(C_1-C_4)$-alkyl, phenyl-$(C_1-C_4)$-alkanoyl or benzoyl, the phenyl radicals in each case being unsubstituted or substituted by one, two or three radicals from the group comprising $(C_1-C_4)$-alkyl, $(C_1-C_4)$-alkoxy, $(C_1-C_2)$-alkylenedioxy, F, Cl, Br, $CF_3$ or hydroxyl, R(9) is hydrogen, $(C_1-C_{10})$-alkyl, phenyl or phenyl-$(C_1-C_4)$-alkyl, the phenyl radical in each case being unsubstituted or substituted by one, two or three radicals from the group comprising $(C_1-C_4)$-alkyl, $(C_1-C_4)$-alkoxy, $(C_1-C_2)$-alkylenedioxy, F, Cl, Br, $CF_3$ or hydroxyl, R(10) is hydrogen, hydroxyl or $(C_1-C_4)$-alkoxy, and R(11) and (R12) or R(13) and R(14) are identical or different and independently of one another are hydrogen, straight-chain or branched $(C_1-C_{10})$-alkyl, $(C_1-C_6)$-alkanoyl, phenyl-$(C_1-C_4)$-alkyl, benzhydryl or benzhydryl-$(C_1-C_4)$-alkyl, phenyl-$(C_1-C_4)$-alkanoyl or benzoyl, the phenyl radicals in each case being unsubstituted or substituted by one, two or three radicals from the group comprising $(C_1-C_4)$-alkyl, $(C_1-C_4)$-alkoxy, $(C_1-C_2)$-alkylenedioxy, F, Cl, Br, $CF_3$ or hydroxyl, and to salts of the compounds of the formula I with pharmaceutically acceptable acids.

Those compounds of the formula I are preferred in which R(1) and R(1)' are identical or different and independently of one another are hydrogen, methyl, ethyl, methoxy, ethoxy, fluorine, chlorine, $CF_3$, nitro or acetamido, R(1)" is hydrogen, R(2) is hydrogen, straight-chain or branched $(C_1-C_6)$-alkyl, allyl, methallyl, benzyl, phenethyl, 4-methoxybenzyl, 3,4-dimethoxybenzyl, 3,4,5-trimethoxybenzyl or 3,4-methylenedioxybenzyl, R(3) is hydrogen, straight-chain or branched $(C_1-C_{12})$-alkyl, allyl, methallyl, $(C_5-C_7)$-cycloalkyl, $(C_5-C_7)$-cycloalkyl-$(C_1-C_4)$-alkyl, benzyl, methylbenzyl, fluorobenzyl, methoxybenzyl, dimethoxybenzyl or phenylethyl, R(4) is hydrogen, methyl, methoxy, ethoxy, chlorine, nitro, hydroxyl, acetamido or amino, R(4)' is hydrogen, A is the group —(CH$_2$)$_m$—O—(CH$_2$)$_n$—, m and n each being 2 or 3, or one of the groups —(CH$_2$)$_p$—CH(OH)—(CH$_2$)$_q$— and —(CH$_2$)$_p$—CH(OCH$_3$)—(CH$_2$)$_q$, p and q each being 1, 2 or 3, or the group —(CH$_2$)$_r$—O—CH$_2$—CO— in which r can be 2 or 3, or the group —(CH$_2$)$_s$—CO—, s being 1, 2, 3 or 4, R(5) is one of the following groups

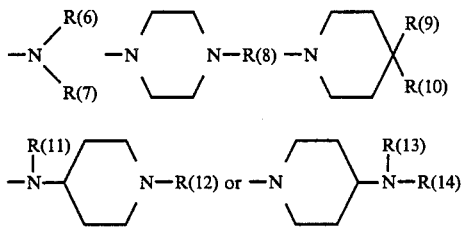

in which

R(6) is hydrogen, methyl, ethyl, propyl or isopropyl,

R(7) is hydrogen, methyl, ethyl, propyl, isopropyl, cyclopentylethyl, cyclohexylethyl, phenyl-(C$_1$-C$_4$)-alkyl, benzhydryl or benzhydryl-(C$_1$-C$_4$)-alkyl, the phenyl radicals in each case being unsubstituted or substituted by one, two or three radicals from the group comprising (C$_1$-C$_4$)-alkyl, (C$_1$-C$_4$)-alkoxy, (C$_1$-C$_2$)-alkylenedioxy, F, Cl, CF$_3$ or hydroxyl, or pyridyl-(C$_1$-C$_4$)-alkyl, R(8) is hydrogen, straight-chain or branched (C$_1$-C$_6$)-alkyl, (C$_1$-C$_6$)-alkanoyl, phenyl, it being possible for the phenyl radical to be substituted by one or two radicals from the group comprising (C$_1$-C$_4$)-alkyl, (C$_1$-C$_4$)-alkoxy, (C$_1$-C$_2$)-alkylenedioxy, F, Cl, CF$_3$ or hydroxyl, phenyl-(C$_1$-C$_4$)-alkyl, phenyl-(C$_3$-C$_5$)-alkenyl, benzhydryl or benzhydryl-(C$_1$-C$_4$)-alkyl, phenyl-(C$_1$-C$_4$)-alkanoyl or benzoyl, the phenyl radicals in each case being unsubstituted or substituted by one, two or three radicals from the group comprising methyl, ethyl, methoxy, ethoxy, (C$_1$-C$_2$)-alkylenedioxy, F, Cl, CF$_3$ or hydroxyl, R(9) is phenyl or phenyl-(C$_1$-C$_4$)-alkyl, the phenyl radical in each case being unsubstituted or substituted by one, two or three radicals from the group comprising (C$_1$-C$_4$)-alkyl, (C$_1$-C$_4$)-alkoxy, (C$_1$-C$_2$)-alkylenedioxy, F, Cl, CF$_3$ or hydroxyl, R(10) is hydrogen, hydroxyl or methoxy, and R(11), R(12), R(13) and R(14) are identical or different and are hydrogen, (C$_1$-C$_8$)-alkyl, (C$_1$-C$_6$)-alkanoyl, phenyl-(C$_1$-C$_4$)-alkyl, benzhydryl or benzhydryl-(C$_1$-C$_4$)-alkyl, the phenyl radicals in each case being unsubstituted or substituted by one, two or three radicals from the group comprising methyl, ethyl, methoxy, ethoxy, (C$_1$-C$_2$)-alkylenedioxy, F, Cl, CF$_3$ or hydroxyl, or are phenyl-(C$_1$-C$_4$)-alkanoyl or benzoyl, the phenyl radicals in each case being unsubstituted or substituted by one, two or three radicals from the group comprising methyl, ethyl, methoxy, ethoxy, (C$_1$-C$_2$)-alkylenedioxy, F, Cl, CF$_3$ or hydroxyl, as well as the salts of these compounds of formula I with pharmaceutically acceptable acids.

Those compounds of the formula I are particularly preferred in which

R(1) is hydrogen, methyl, methoxy, fluorine or chlorine,

R(1)' is hydrogen or methoxy,

R(1)' is hydrogen,

R(2) is hydrogen, methyl, ethyl, propyl, mbutyl, sec.-butyl, isobutyl, benzyl or phenethyl, R(3) is hydrogen, straight-chain or branched (C$_1$-C$_{12}$)-alkyl, cyclopentyl, cyclohexyl, cyclopentylmethyl, cyclohexylmethyl, allyl, methallyl, benzyl, methylbenzyl, fluorobenzyl, methoxybenzyl, dimethoxybenzyl or phenylethyl, R(4) is hydrogen, methoxy, methyl, chlorine, nitro or hydroxyl, R(4)' is hydrogen, A is the group —(CH$_2$)$_m$—O—(CH$_2$)$_n$—, m and n each being 2 or 3, or one of the groups —(CH$_2$)$_p$—CH(OH)—(CH$_2$)$_q$— and —(CH$_2$)$_p$—CH(OCH$_3$)—(CH$_2$)$_q$, p being 1 or 2 and q being 1, or the group —(CH$_2$)$_r$—O—CH$_2$—CO—, r being 2 or 3, or the group —(CH$_2$)$_s$—CO—, s being 3 or 4, R(5) is one of the following groups

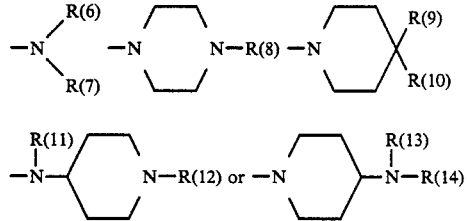

in which

R(6) is hydrogen or methyl,

R(7) is phenyl-(C$_1$-C$_4$)-alkyl, benzhydryl or benzhydryl-(C$_1$-C$_4$)-alkyl, the phenyl radical in each case being unsubstituted or substituted by one, two or three radicals from the group comprising methyl, methoxy, fluorine, chlorine, methylenedioxy or hydroxyl, R(8) is straight-chain or branched (C$_1$-C$_6$)-alkyl, (C$_1$-C$_6$)-alkanoyl, phenyl, phenyl-(C$_1$-C$_4$)-alkyl, benzhydryl or benzhydryl-(C$_1$-C$_4$)-alkyl, phenyl-(C$_1$-C$_4$)-alkanoyl or benzoyl, the phenyl radicals in each case being unsubstituted or substituted by one, two or three radicals from the group comprising methyl, methoxy, ethoxy, methylenedioxy, fluorine, chlorine or hydroxyl, R(9) is phenyl, the phenyl radical being unsubstituted or substituted by one, two or three radicals from the group comprising methyl, methoxy, fluorine, chlorine, methylenedioxy or hydroxyl, R(10) is hydrogen, hydroxyl or methoxy, and R(10) is hydrogen, hydroxyl or methoxy, and R(11), R(12), R(13) and R(14) are identical or different and are hydrogen, (C$_1$-C$_6$)-alkyl, (C$_1$-C$_6$)-alkanoyl, phenyl-(C$_1$-C$_4$)-alkyl, benzhydryl or benzhydryl-(C$_1$-C$_4$)-alkyl, phenyl-(C$_1$-C$_4$)-alkanoyl or benzoyl, the phenyl radicals in each case being unsubstituted or substituted by one, two or three radicals from the group comprising methyl, methoxy, methylenedioxy, fluorine, chlorine or hydroxyl, as well as the salts of these compounds of the formula I with pharmaceutically acceptable acids.

Such pharmaceutically acceptable acids can be inorganic acids, such as hydrochloric acid, hydrobromic acid, hydriodic acid, sulfuric acid, phosphoric acid or nitric acid, or organic acids, such as tartaric acid, malic acid, lactic acid, maleic acid, fumaric acid, malonic acid, oxalic acid, gluconic acid, camphorsulfonic acid, benzenesulfonic acid, acetic acid, propionic acid or p-toluenesulfonic acid.

The compounds of the formula I have asymmetric carbon atoms and can therefore be in the form of enantiomers or diastereomers. The invention comprises both the pure isomers and their mixtures. These mixtures of diastereomers can be separated into the components by usual methods, for example by selective crystallization from suitable solvents or chromatography on silica gel or alumina. Racemates can be resolved into the individual enantiomers by usual methods, such as, for example, by forming a salt with optically active acids, such as camphorsulfonic acid or dibenzoyltartaric acid, and selective crystallization, or by forming derivatives with suitable optically active reagents, separation of the diastereomeric derivatives and redissociation.

The invention also relates to processes for the preparation of compounds of the formula I, which comprise (a) reacting a compound of the formula II

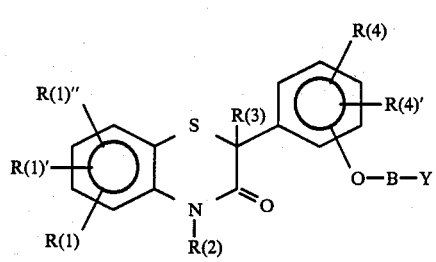

in which R(1), R(1)', R(1)'', R(2), R(3), R(4) and R(4)' have the same meaning as in the formula I and in which B represents the radicals —(CH₂)ₘ—O—(CH₂)ₙ or —(CH₂)ₚ—CH(OH)—(CH₂)_q, m, n, p and q having the same meaning as in the formula I, and in which Y is a leaving group which can be displaced by a nucleophilic reaction, in particular a chlorine, bromine or iodine atom, a sulfonic acid radical, preferably a methanesulfonyl radical, a benzenesulfonyl radical, a toluenesulfonyl radical or a trifluoromethanesulfonyl radical, with one of the compounds of the formulae IIIa, IIIb, IIIc, IIId or IIIe

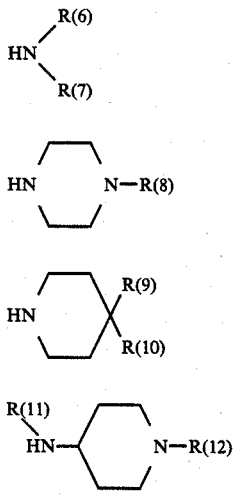

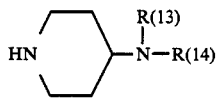

in which R(6), R(7), R(8), R(9), R(10), R(11), R(12), R(13) and R(14) have the same meaning as in the formula I, under the conditions of nucleophilic substitution, preferably in a polar organic solvent such as an alcohol, preferably methanol, ethanol, propanol or isopropanol, or a lower ketone, preferably acetone or methyl ethyl ketone, or dimethylformamide, dimethyl sulfoxide or sulfolan or a hydrocarbon, preferably toluene, in the presence or absence of an auxiliary base for intercepting the acid being formed, preferably in the presence of potassium carbonate, sodium carbonate, triethylamine, N-ethylmorpholine or pyridine, at a temperature between 0° and 160° C., preferably between 20° and 120° C., or (b) reacting a compound of the formula IV

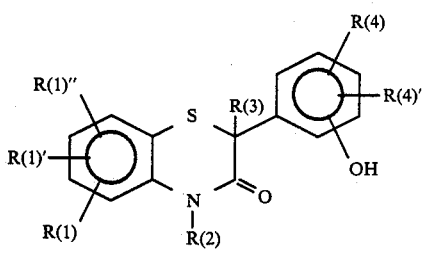

in which R(1), R(1)', R(1)'', R(2), R(3), R(4) and R(4)' have the same meaning as in the formula I, with a compound of the formula V

Z—A—R(5)   V in which Z is as defined for Y in the formula II and in which R(5) and A have the same meaning as in the formula I, either in a polar aprotic solvent such as dimethylformamide, dimethyl sulfoxide, tetrahydrofuran, sulfolan or N-methylpyrrolidone, in the presence of a strong base such as sodium hydride, potassium hydride, sodium amide, lithium diisopropylamide, butyllithium or lithium hexamethyldisilazide, at a temperature between −40° and +60° C., preferably between −10° and −30° C., or in a protic or aprotic polar organic solvent such as a lower alcohol, for example methanol, ethanol or isopropanol, or a lower ketone, preferably acetone or methyl ethyl ketone, or in dimethylformamide, in the presence of a weak to moderately strong base such as an alkali metal or alkaline earth metal hydroxide or carbonate or an amine such as, for example, triethylamine, N-ethylmorpholine, N-methyldiisopropylamine or pyridine, at a temperature between 0° and 160° C., preferably between 20° and 120° C., or (c) reacting a compound of the formula VI

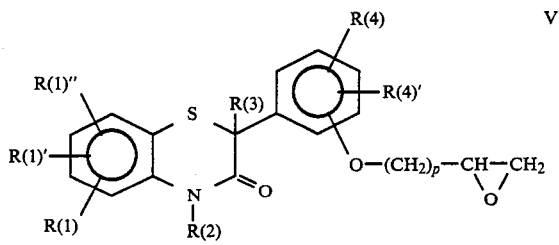

in which R(1), R(1)′, R(1)″, R(2), R(3), R(4), R(4)′ and p have the same meaning as in the formula I, with amines of the formula IIIa–IIIe without a solvent or in the presence of a preferably polar solvent such as methanol, isopropanol, acetone, THF or dimethylformamide, compounds of the formula I being formed in which A is $(CH_2)_p$—CH(OH)—$CH_2$, or (d) reacting a compound of the formula VII

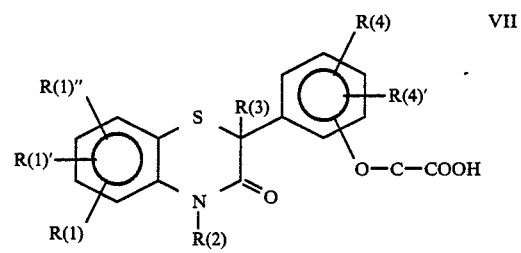

in which R(1), R(1)′, R(1)″, R(2), R(3), R(4) and R(4)′ have the same meaning as in the formula I and in which C represents the radicals —$(CH_2)_r$—O—$CH_2$—CO— or —$(CH_2)_s$—CO—, r and s having the same meaning as in the formula I, with one of the compounds of the formulae IIIa, IIIb, IIIc, IIId or IIIe under the amide formation conditions known from the literature, compounds of the formula I being formed in which A is —$(CH_2)_r$—O—$CH_2$CO— or —$(CH_2)_s$—CO—. Compounds of formula II are obtained from compounds of the formula IV and compounds of the formula VIII $$Z—B—Y \qquad VIII$$

in which B and Y have the same meaning as in the formula II and Z is a leaving group which can be displaced by a nucleophilic reaction, Z being as defined for Y and being identical to or different from Y, under the conditions described under (b).

Compounds of formula VI are obtained from compounds of the formula IV, for example with epichlorohydrin and bases (for p=1) by known methods, or by alkylation of compounds of the formula IV with compounds of the formula IX $$Y—(CH_2)_p—CH=CH_2 \qquad IX$$

in which p has the same meaning as in the formula I and Y has the same meaning as in the formula II, compounds of the formula X

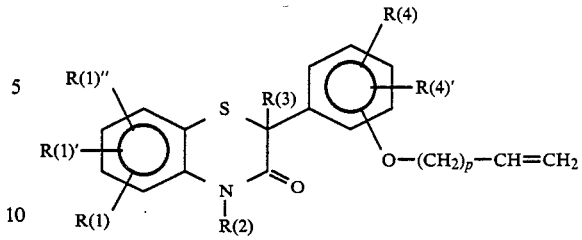

being formed, in which R(1), R(1)′, R(1)″, R(2), R(3), R(4), R(4)′ and p have the same meaning as in the formula I. Subsequent epoxidation of the compounds X by known methods, for example with m-chloroperbenzoic acid in methylene chloride, gives compounds of the formula VI.

Compounds of the formula VII are obtained from compounds of the formula IV and compounds of the formula XI $$Y—C—COOR(15) \qquad XI$$

in which Y has the same meaning as in the formula II and C has the same meaning as in the formula VII and R(15) is hydrogen, a straight-chain or branched ($C_1$–$C_5$)-alkyl group or a benzyl group which is unsubstituted or substituted by methoxy or nitro, under the conditions described under process variant (b) and, if appropriate, subsequent elimination of the ester radical R(15) under conditions known from the literature, for example catalytic hydrogenation or alkaline saponification.

Compounds of the formula IV are known from EP-A-146,893.

Unless explicitly stated otherwise, alkyl, alkylene, alkanoyl and alkoxy always denote straight or branched chains.

The compounds according to the invention, of the formula I, show hypotensive, in particular calcium-antagonistic actions and can therefore be used for the treatment of all pathological conditions which are caused by a disturbance in the calcium balance of a warm-blooded animal.

Their calcium-antagonistic activity can be demonstrated by the displacement of tritium-labeled nitrendipin as a biological test model.

For this purpose, membrane preparations which contain isolated calcium channels are charged with the labeled substance. After incubation with the test substance, the released radioactivity in the supernatant solution is determined. In this model, the compounds according to the invention, of the formula I, show $IC_{50}$ values of $10^{-6}$ molar to $10^{-10}$ molar. In further test models, by means of which a calcium-antagonistic action can be demonstrated, for example by the coronary blood flow in the isolated guinea pig heart or by the action potential of the isolated guinea pig papillary muscle, the compounds of the formula I likewise show a strong action.

The compounds according to the invention, of the formula I, and their pharmacologically acceptable salts reduce the influx of calcium ions into cells and are therefore suitable for treating the cardiovascular system in the case of the relevant complaints, for example various forms of angina pectoris, tachycardia, heart arrhythmias and high blood pressure. They are active within a wide dose range. The level of the dose administered depends on the nature of the desired treatment, on the manner of administration and on the condition, type and size of the mammal treated. In oral dosage, satisfactory results are obtained with quantities of from 0.01 mg, preferably from 0.1 mg and up to 100 mg, preferably up to 20 mg, of a compound of the formula I per kg of body weight. In man, the daily dose varies between 10 and 800 mg, preferably 20 to 500 mg, and single doses of 5 to 200 mg can be given, preferably once to three times daily.

For intravenous and intramuscular administration, the daily dose is 1 to 300 mg, preferably 5 to 150 mg.

The pharmacologically usable compounds of the present invention and their salts can be used for the preparation of pharmaceutical products which contain an active amount of the active substance together with excipients and which are suitable for enteral and parenteral administration. Preferably, tablets or gelatine capsules are used, which contain the active compound together with diluents, for example lactose, dextrose, sucrose, mannitol, sorbitol, cellulose and/or glycine and lubricants such as siliceous earth, talc, stearic acid or salts thereof, such as magnesium or calcium stearate, and/or polyethylene glycol. Tablets also contain binders such as magnesium aluminum silicate, starch, gelatine, tragacanth, methylcellulose, sodium carboxymethylcellulose and/or polyvinylpyrrolidone and, if necessary, dyes, flavorings and sweeteners. Injectable solutions are preferably isotonic aqueous solutions or suspensions, which can have been sterilized and can contain auxiliaries such as preservatives, stabilizers, wetting agents and/or emulsifiers, solubilizers, salts for regulating the osmotic pressure and/or buffer substances. The pharmaceutical products according to the invention which, if desired, can contain further pharmacologically valuable substances, are prepared, for example, by means of conventional mixing, granulating and tableting processes and contain 0.1% to about 75%, preferably about 1% to about 50, of active compound.

The examples which now follow are intended to illustrate the invention without restricting it to these examples.

EXAMPLE 1

3,4-Dihydro-2-isopropyl-4-methyl-2-[2-(5-bromo-3-oxapentyloxy)-phenyl]-2H-1,4-benzothiazin-3-one 9.4 g (30 mmol) of 3,4-dihydro-2-isopropyl-4-methyl-2-(2-hydroxyphenyl)-2H-1,4-benzothiazin-3-one are boiled for 8 hours under reflux with 22 g (94 mmol) of 1,5-dibromo-3-oxapentane and 12.9 g (90 mmol) of potassium carbonate in 75 ml of 2-butanone. The mixture is then filtered with suction, and the filtrate is concentrated, finally in a high vacuum. This gives 12.4 g of an almost colorless oil.

$^1$H-NMR (CDCl$_3$): δ=7.5–6.5 (m, 8H), 4.0–3.3 (m, 8H), 3.4 (s, 3H), 2.9 (septet, 1H); 1.15+0.95 (2d, 6H) ppm.

EXAMPLE 2

3,4-Dihydro-2-isopropyl-4-methyl-2-[2-[5-[4-[2-(3,4,5-trimethoxyphenyl)-ethyl]-piperazinyl]-3-oxapentyloxy]-phenyl]-2H-1,4-benzothiazin-3-one dihydrochloride 4.1 g (88 mmol) of the compound from Example 1 are heated to the boil for 8 hours with 1.2 g of potassium carbonate and 8 g of 2-(3,4,5-trimethoxyphenyl)-ethyl-piperazine in 100 ml of isopropanol. After cooling, the product is filtered with suction and the filtrate is concentrated. Chromatography on 300 g of silica gel given 4.7 g of a colorless oil.

$^1$H-NMR (CDCl$_3$): δ=7.5–6.5 (m, 8H), 6.38 (s, 2H), 4.1–3.5 (m, 6H), 3.8 (s, 9H), 3.4 (s, 3H); 3.0–2.4 (m, 16H); 1.13+0.95 (2d, 6H).

The free base is dissolved in methanol and treated with ethereal hydrochloric acid. After concentrating, the product is recrystallized from isopropanol/ether. This gives 3.1 g of the dihydrochloride of melting point 191°–192° C.

Calculated: C$_{37}$H$_{49}$N$_3$O$_6$S.2HCl.H$_2$O C 58.9 H 7.08 N 5.6 Cl 9.4; Found: C 59.0 H 7.2 N 5.5 Cl 10.1.

EXAMPLE 3

3,4-Dihydro-2-isopropyl-4-methyl-2-[2-[5-[4-[4,4-bis-(4-fluorophenyl)-butyl]-piperazinyl]-3-oxapentyloxy]-phenyl]-2H-1,4-benzothiazin-3-one dihydrochloride 4.1 g (88 mmol) of the compound from Example 1 were heated under reflux for 8 hours with 1.2 g of potassium carbonate and 5.6 g of 4,4-bis-(4-fluorophenyl)-butyl-piperazine in 100 ml of isopropanol. Working up as in Example 2 gives 2.8 g of a colorless oil.

$^1$H-NMR (CDCl$_3$): δ=7.5–6.4 (m, 16H); 4.1–3.6 (m, 7H); 3.4 (s, 3H); 3.0–1.8 (m, 17H); 1.08+0.95 (2d, 6H) ppm.

The dihydrochloride is obtained by treating the methanolic solution of the free base with ethereal HCl and concentrating. Melting point 110° C., yield 3.6 g.

Calculated: C$_{42}$H$_{49}$N$_3$O$_3$F$_2$S.2HCl.CH$_3$OH C 62.3 H 6.7 N 5.1; Found: C 61.6 H 6.6 N 4.8.

EXAMPLE 4

3,4-Dihydro-2-isopropyl-4-methyl-2-[2-[5-[N-methyl-N-[2-(3,4-dimethoxyphenyl)]-ethyl]-3-oxapentyloxy]-phenyl]-2H-benzothiazin-3-one hydrochloride 4.1 g (8.8 mmol) of the compound from Example 1 are reacted with 1.2 g of potassium carbonate and 3.4 g of N-methyl-homoveratrylamine by the procedure described in Example 2. This gives 2.2 g of the free base as an oil.

$^1$H-NMR (CDCl$_3$): δ=7.5–6.5 (m, 11H); 4.05–3.6 (m, 6H); 3.88+3.80 (2s, 6H); 3.4 (s, 3H); 3.1–2.7 (m, 6H); 2.6 (s, 3H); 1.15+0.9 (2d, 6H) ppm.

The hydrochloride is obtained as a viscous resin by adding ethereal HCl and concentrating.

EXAMPLE 5

3,4-Dihydro-2-isopropyl-4-methyl-2-[2-(oxiranyl-methoxy)phenyl]-2H-1,4-benzothiazin-3-one 4.7 g (15.0 mmol) of 3,4-dihydro-2-isopropyl-4-methyl-2-(2-hydroxyphenyl)-2H-1,4-benzothiazin-3-one are stirred for 24 hours at 85° C. with 0.6 g of NaOH, 2 ml of H$_2$O and 50 ml of epichlorohydrin. After dilution with water, the mixture is extracted with methylene chloride, and the extract is dried with sodium sulfate and concentrated. This gives 5.3 g of the title compound as a colorless oil.

$^1$H-NMR (CDCl$_3$): δ=7.6–6.4 (m, 8H); 4.2–3.8 (m, 3H); 3.4 (s, 3H); 3.4–2.5 (m, 4H); 1.4–0.7 (m, 6H) ppm.

EXAMPLE 6

3,4-Dihydro-2-isopropyl-4-methyl-2-[2-[2-hydroxy-3-[4-[2-(3,4,5-trimethoxyphenyl)-ethyl]-piperazinyl]-propoxy]-phenyl]-2H-1,4-benzothiazin-3-one dihydrochloride 3 g of the compound from Example 5 are stirred under reflux for 24 hours with 6.8 g (24 mmol) of 2-(3,4,5-trimethoxyphenyl)-ethyl-piperazine in 50 ml of methanol. After column chromatography on 300 g of silica gel, 18 g of the free base are obtained as an oil.

$^1$H-NMR (CDCl$_3$) δ=7.5–6.5 (m, 8H); 6.45 (s, 2H); 4.1–3.4 (m, 5H); 3.8 (s, 9H); 3.45 (s, 3H); 3.1–2.4 (m, 13H); 1.25+0.9 (2d, 6H) ppm.

The hydrochloride is precipitated from methanolic solution with ethereal hydrochloric acid and recrystallized from ethanol; melting point 236°–237° C. (decomposition).

EXAMPLE 7

3,4-Dihydro-2-isopropyl-4-methyl-2-[2-[2-hydroxy-3-[4-[4,4-bis-(4-fluorophenyl)-butyl]-piperazinyl]-propoxy]-phenyl]-2H-1,4-benzothiazin-3-one dihydrochloride 4.4 g (12 mmol) of the compound from Example 5 are reacted with 7.9 g of 4,4-bis-(4-fluorophenyl)-butyl-piperazine by the procedure described in Example 6. This gives 2.7 g of the free base as an oil.

$^1$H-NMR (CDCl$_3$): δ=7.5–6.5 (m, 16H); 4.3–3.6 (m, 6H); 3.4 (s, 3H); 2.8–2.0 (m, 14H); 1.5–0.7 (m, 6H) ppm.

Dihydrochloride: colorless crystals, melting point 85° C. (decomposition).

EXAMPLE 8

3,4-Dihydro-2-isopropyl-4-methyl-2-[2-[2-hydroxy-3-[-4-[3-(3,4,5-trimethoxyphenyl)-propyl]-piperazinyl]-propoxy]-phenyl]-2H-1,4-benzothiazin-3-one dihydrochloride 5.5 g (15 mmol) of the compound from Example 5 are reacted with 6.6 g (22 mmol) of 3-(3,4,5-trimethoxyphenyl)-propyl-piperazine by the procedure described in Example 5. Free base: colorless oil, yield 3.9 g $^1$H-NMR (CDCl$_3$): δ=7.5–6.5 (m, 8H); 6.38 (s, 2H); 4.2–3.6 (m, 5H); 3.75 (s, 9H); 3.4 (s, 3H); 2.8–2.4 (m, 13H); 2.2–1.7 (m, 2H); 1.15+0.8 (2d, 6H) ppm.

Dihydrochloride: colorless crystals, melting point 105° C.

EXAMPLE 9

7-Chloro-3,4-dihydro-2-isopropyl-4-methyl-2-[2-(oxiranylmethoxy)-phenyl]-2H-benzothiazin-3-one 3 g of 7-chloro-3,4-dihydro-2-isopropyl-4-methyl-2-(2-hydroxyphenyl)-2H-1,4-benzothiazin-3-one are added to a suspension of 0.6 g of NaH (50% in oil) in 40 ml of dimethylformamide. After 15 minutes, 2 ml of epichlorohydrin are added, and the mixture is stirred for 20 hours at 20° C. After dilution with ethyl acetate, the mixture is washed 3 times with water and once with saturated sodium chloride solution, dried with sodium sulfate and concentrated. The diastereomers are separated by chromatography on silica gel (phase 1:4 ethyl acetate/cyclohexane).

Isomer 1: Yield 1.49 g; Rf: 0.4 (1:1 ethyl acetate/cyclohexane); Melting point 123°–125° C. (from ethanol/hexane).

$^1$H-NMR (CDCl$_3$): δ=7.6–6.5 (m, 7H); 4.3–3.5 (m, 3H); 3.45 (s, 3H); 3.0–2.4 (m, 3H); 1.1+0.95 (2d, 6H) ppm.

Isomer 2: Yield 1.35 g; Rf: 0.35 (1:1 ethyl acetate/cyclohexane); Melting point 107°–108° C. (from ethanol/hexane).

$^1$H-NMR (CDCl$_3$): δ=7.6–6.6 (m, 7H); 4.3–3.6 (m, 2H); 3.5–3.2 (m, 1H); 3.4 (s, 3H); 3.0–2.5 (m, 2H); 1.1+0.97 (2d, 6H) ppm.

EXAMPLE 10

7-Chloro-3,4-dihydro-2-isopropyl-4-methyl-2-[2-[2-hydroxy-3-[4-[2-(3,4,5-trimethoxyphenyl)-ethyl]-piperazinyl]-propoxy]-phenyl]-2H-1,4-benzothiazin-3-one dihydrochloride (Isomer 1)

1.2 g of isomer 1 from Example 9 are boiled under reflux for 8 hours with 1.5 g of 2-(3,4,5-trimethoxyphenyl)ethyl-piperazine dihydrochloride and 1.5 g of potassium carbonate in 30 ml of isopropanol. After cooling, the mixture is filtered and concentrated. Chromatography on silica gel with 20:1 methylene chloride/methanol gives 1.8 g of colorless oil.

$^1$H-NMR (CDCl$_3$): δ=7.5–6.65 (m, 7H); 6.44 (s, 2H); 4.28 (s, 1H); 4.0–3.9 (m, 1H); 3.86+3.80 (2s, 9H); 3.8–3.65 (m, 2H); 3.42 (s, 3H); 3.1 (m, 1H); 2.85–2.45 (m, 14H); 1.25+0.78 (2d, 6H) ppm.

The free base is dissolved in acetone, treated with 3 ml of ethanolic HCl, concentrated, and twice more concentrated with acetone. After the mixture has been left to stand in acetone, the crystals are filtered off with suction. Melting point 215°–219° C., yield 1.54 g.

Calculated: C$_{36}$H$_{46}$ClH$_3$O$_6$S.2HCl.½H$_2$O C 56,4 H 6,6 N 5,5 Found: C 56,5 H 6,5 N 5,0.

EXAMPLE 11

7-Chloro-3,4-dihydro-2-isopropyl-4-methyl-2-[2-[2-hydroxy-3-[4-[2-(3,4,5-trimethoxyphenyl)-ethyl]-piperazinyl]-propoxy]-phenyl]-2H-1,4-benzothiazin-3-one dihydrochloride (Isomer 2)

0.9 g of the isomer from Example 9 is reacted with 1.3 g of 2-(3,4,5-trimethoxyphenyl)-ethyl-piperazine dihydrochloride and 1.3 g of potassium carbonate in 25 ml of isopropanol by the procedure given in Example 10. This gives 1.25 g of the free base as an oil.

$^1$H-NMR (CDCl$_3$): δ=7.6–6.5 (m, 7H); 6.45 (s, 2H); 4.3–3.5 (m, 4H); 3.85 (s, 9H); 3.45 (s, 3H); 3.2–2.4 (m, 15H); 1.2+0.8 (2d, 6H) ppm.

Dihydrochloride: amorphous powder.

EXAMPLE 12

7-Chloro-3,4-dihydro-2-isopropyl-4-methyl-2-[2-[2-methoxy-3-[4-[2-(3,4,5-trimethoxyphenyl)-ethyl]-piperazinyl]-propoxy]-phenyl]-2H-1,4-benzothiazin-3-one dihydrochloride (Isomer 1)

0.75 g of the compound from Example 10 is added to a suspension of 0.5 g of sodium hydride (50% in oil) in 15 ml of DMF. After 10 minutes, 70 μl of methyl iodide are added, and the mixture is stirred for 3 hours. After dilution with ethyl acetate, the mixture is washed 4 times with water, dried with sodium sulfate and concentrated. This gives 0.38 g of an oil.

$^1$H-NMR (CDCl$_3$): δ=7.6–6.5 (m, 7H); 6.4 (s, 2H); 4.3–3.5 (m, 4H); 3.8 (s, 9H); 3.55 (s, 3H); 3.45 (s, 3H); 3.2–2.4 (m, 15H); 1.15+0.9 (2d, 6H) ppm.

Dihydrochloride: colorless crystals, melting point 237°–240° C.

EXAMPLE 13

7-Chloro-3,4-dihydro-2-isopropyl-4-methyl-2-[2-[2-methoxy-3-[4-[2-(3,4,5-trimethoxyphenyl)-ethyl]-piperazinyl]-propoxy]-phenyl]-2H-1,4-benzothiazin-3-one dihydrochloride (Isomer 2)

0.7 g of the compound from Example 11 is reacted with 0.5 g of sodium hydride (50% in oil) and 70 μl of methyl iodide in accordance with the instructions given in Example 12. This gives 0.6 g of the title compound as a colorless amorphous powder.

EXAMPLE 14

4-[(4-Methyl-2-isopropyl-3,4-dihydro-2H-1,4-benzothiazin-3-on-2-yl)-2-phenoxy]-butyric acid 4-[2-(3,4,5-trimethoxyphenyl)-ethyl]-piperazide hydrochloride (a) 15.7 g of 3,4-dihydro-2-isopropyl-4-methyl-2-(2-hydroxyphenyl)-2H-1,4-benzothiazin-3-one are stirred under reflux for 8 hours with 6.9 g of potassium carbonate and 8 ml of ethyl 4-bromobutyrate in 150 ml of 2-butanone. After filtration with suction, the filtrate is concentrated. This gives 19.8 g of ethyl 4-[(4-methyl-2-isopropyl-3,4-dihydro-2H-1,4-benzothiazin-3-on-2-yl)-2-phenoxy]-butyrate.

$^1$H-NMR (CDCl$_3$): δ=7.5–6.4 (m, 8H); 4.1 (q, 2H); 3.8 (t, 2H); 3.4 (s, 3H); 3.2–2.0 (m, 5H); 1.4–0.7 (2d+t, 9H) ppm.

(b) 21.4 g of the ester from (a) are boiled under reflux for 3 hours in 250 ml of ethanol with 3.35 g of KOH. After concentration, the residue is taken up in a little water and extracted twice with ethyl acetate. The aqueous phase is acidified with HCl and extracted 3 times with ethyl acetate, and the ethyl acetate phases are dried with sodium sulfate and concentrated. This gives 118 g of 4-[(4-methyl-2-isopropyl-3,4-dihydro-2H-1,4-benzothiazin-3-on-2-yl)-2-phenoxy]-butyric acid of melting point 131°–133° C. (recrystallized from toluene).

Calculated: $C_{22}H_{25}NO_4S$ C 66.1 H 6.3 N 3.5; Found: C 65.7 H 6.4 N 3.5.

(c) 2 ml of a 30% solution of 1-hydroxybenzotriazole in DMF are added to 6 g (15 mmol) of the carboxylic acid from (b) in 20 ml of DMF. At room temperature, 4.2 g (15 mmol) of 2-(3,4,5-trimethoxyphenyl)-ethyl-piperazine and 3.7 g (18 mmol) of dicyclohexylcarbodiimide are added. After 14 hours at room temperature, the mixture is filtered with suction, 200 ml of ice water are added to the solution and the latter is extracted (3 times) with ethyl acetate. The combined organic phases are washed once with saturated sodium bicarbonate solution and once with water, dried with sodium sulfate and concentrated. Chromatography on 250 g of silica gel with 9:1 methylene chloride/methanol gives the free base.

$^1$H-NMR (CDCl$_3$): δ=7.5–6.5 (m, 8H); 6.4 (s, 2H); 4.2–3.5 (m, 4H); 3.8 (s, 9H); 3.4 (s, 3H); 3.1–2.0 (m, 15H); 1.15+0.95 (2d, 6H) ppm.

Hydrochloride: yield 5.3 g, melting point 138°–140° C.

Calculated: $C_{37}H_{47}N_3O_6S \cdot HCl$ C 62.6 H 6.9 N 6.0; Found: C 62.3 H 7.0 N 6.0.

We claim:

1. A compound of the formula I

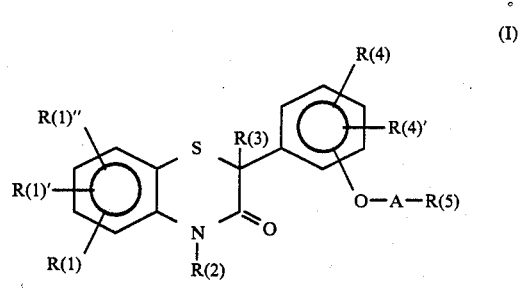

in which

R(1), R(1)′ and R(1)″ are identical or different and independently of one another are hydrogen, $(C_1-C_4)$-alkyl, $(C_1-C_3)$-alkoxy, F, Cl, Br, $CF_3$, nitro, hydroxyl, acetamido or amino, R(2) is hydrogen, straight-chain or branched $(C_1-C_{10})$-alkyl, straight-chain or branched $(C_3-C_{10})$-alkenyl or phenyl-$(C_1-C_4)$-alkyl, the phenyl ring being unsubstituted or substituted by one, two or three substituents from the group comprising $(C_1-C_4)$-alkyl, $(C_1-C_3)$-alkoxy, F, Cl, $CF_3$, $(C_1-C_2)$-alkylenedioxy or nitro, R(3) is straight-chain or branched $(C_1-C_{15})$-alkyl, straight-chain or branched $(C_3-C_{15})$-alkenyl, $(C_4-C_8)$-cycloalkyl, $(C_4-C_8)$-cycloalkyl-$(C_1-C_4)$-alkyl, phenyl, or phenyl-$(C_1-C_4)$-alkyl, the phenyl radical being unsubstituted or substituted by one, two or three substituents from the group comprising $(C_1-C_4)$-alkyl, $(C_1-C_3)$-alkoxy, F, Cl, $CF_3$, $(C_1-C_2)$-alkylenedioxy or nitro, R(4) and R(4)′ are identical or different and independently of one another are hydrogen, $(C_1-C_4)$-alkyl, $(C_1-C_3)$-alkoxy, F, Cl, $CF_3$, nitro, hydroxyl, acetamido or amino, A is the group $-(CH_2)_m-O-(CH_2)_n-$, m and n each being 2 or 3, or one of the groups $-(CH_2)_p-CH(OH)-(CH_2)_q-$ and $-(CH_2)_p-CH(OCH_3)-(CH_2)_q-$, p and q each being 1, 2 or 3, or the group $-(CH_2)_r-O-CH_2-CO-$, r being 2 or 3, or the group $-(CH_2)_s-CO-$, s being 1, 2, 3 or 4, R(5) is one of the following groups

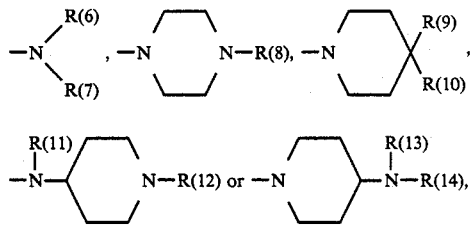

in which

R(6) and R(7) are identical or different and independently of one another are hydrogen, $(C_1-C_{10})$-alkyl, $(C_4-C_8)$-cycloalkyl, $(C_4-C_8)$-cycloalkyl-$(C_1-C_4)$-alkyl, pyridyl-$(C_1-C_4)$-alkyl, phenyl-$(C_1-C_6)$-alkyl, benzhydryl or benzhydryl-$(C_1-C_4)$-alkyl, the phenyl radicals in each case being unsubstituted or substituted by one, two or three radicals from the group comprising $(C_1-C_4)$-alkyl, $(C_1-C_4)$-alkoxy, $(C_1-C_2)$-alkylenedioxy, F, Cl, Br, $CF_3$ or hydroxyl, R(8) is hydrogen, straight-chain or branched ($C_1$-$C_{10}$)-alkyl, ($C_1$-$C_8$)-alkanoyl, pyridyl, pyrimidinyl, phenyl, phenyl-($C_1$-$C_4$)-alkyl, phenyl-($C_3$-$C_5$)-alkenyl, benzyhydryl or benzhydryl-($C_1$-$C_4$)-alkyl, phenyl-($C_1$-$C_4$)-alkanoyl or benzoyl, the phenyl radicals in each case being unsubstituted or substituted by one, two or three radicals from the group comprising ($C_1$-$C_4$)-alkyl, ($C_1$-$C_4$)-alkoxy, ($C_1$-$C_2$)-alkylenedioxy, F, Cl, Br, $CF_3$ or hydroxyl, R(9) is hydrogen, ($C_1$-$C_{10}$)-alkyl, phenyl or phenyl-($C_1$-$C_4$)-alkyl, the phenyl radical in each case being unsubstituted or substituted by one, two or three radicals from the group comprising ($C_1$-$C_4$)-alkyl, ($C_1$-$C_4$)-alkoxy, ($C_1$-$C_2$)-alkylenedioxy, F, Cl, Br, $CF_3$ or hydroxyl, R(10) is hydrogen, hydroxyl or ($C_1$-$C_4$)-alkoxy, and R(11) and R(12) or R(13) and R(14) are identical or different and independently of one another are hydrogen, straight-chain or branched ($C_1$-$C_{10}$)-alkyl, ($C_1$-$C_6$)-alkanoyl, phenyl-($C_1$-$C_4$)-alkyl, benzhydryl or benzhydryl-($C_1$-$C_4$)-alkyl, phenyl-($C_1$-$C_4$)-alkanoyl or benzoyl, the phenyl radicals in each case being unsubstituted or substituted by one, two or three radicals from the group comprising ($C_1$-$C_4$)-alkyl, ($C_1$-$C_4$)-alkoxy, ($C_1$-$C_2$)-alkylenedioxy, F, Cl, Br, $CF_3$ or hydroxyl, and the salts of compound of the formula I with pharmaceutically acceptable acids.

2. A compound of the formula I as claimed in claim 1, wherein

R(1) and R(1)' are identical or different and independently of one another are hydrogen, methyl, ethyl, methoxy, ethoxy, fluorine, chlorine, $CF_3$, nitro or acetamido, R(1)" is hydrogen, R(2) is hydrogen, straight-chain or branched ($C_1$-$C_6$)-alkyl, allyl, methallyl, benzyl, phenethyl, 4-methoxybenzyl, 3,4-dimethoxybenzyl, 3,4,5-trimethoxybenzyl or 3,4-methylenedioxybenzyl, R(3) is straight-chain or branched ($C_1$-$C_{12}$)-alkyl, allyl, methallyl, ($C_5$-$C_7$)-cycloalkyl, ($C_5$-$C_7$)-cycloalkyl-($C_1$-$C_4$)-alkyl, benzyl, methylbenzyl, fluorobenzyl, methoxybenzyl, dimethoxybenzyl or phenylethyl, R(4) is hydrogen, methyl, methoxy, ethoxy, chlorine, nitro, hydroxyl, acetamido or amino, R(4)' is hydrogen, A is the group —$(CH_2)_m$—O—$(CH_2)_n$—, m and n each being 2 or 3, or one of the groups —$(CH_2)_p$—CH(OH)—$(CH_2)_q$— and —$(CH_2)_p$—CH(OCH$_3$)—$(CH_2)_q$, p and q each being 1, 2 or 3, or the group —$(CH_2)_r$' O—$CH_2$—CO— in which r can be 2 or 3, or the group —$(CH_2)_s$—CO—, s being 1, 2, 3 or 4, R(5) is one of the following groups

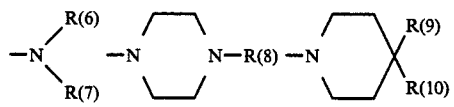

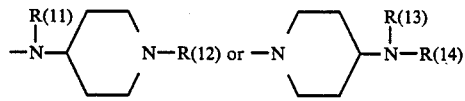

in which

R(6) is hydrogen, methyl, ethyl, propyl or isopropyl,

R(7) is hydrogen, methyl, ethyl, propyl, isopropyl, cyclopentylethyl, cyclohexylethyl, phenyl-($C_1$-$C_4$)-alkyl, benzhydryl or benzhydryl-($C_1$-$C_4$)-alkyl, the phenyl radicals in each case being unsubstituted or substituted by one, two or three radicals from the group comprising ($C_1$-$C_4$)-alkyl, ($C_1$-$C_4$)-alkoxy, ($C_1$-$C_2$)-alkylenedioxy, F, Cl, $CF_3$ or hydroxyl, or pyridyl-($C_1$-$C_4$)-alkyl, R(8) is hydrogen, straight-chain or branched ($C_1$-$C_6$)-alkyl, ($C_1$-$C_6$)-alkanoyl, phenyl, it being possible for the phenyl radical to be substituted by one or two radicals from the group comprising ($C_1$-$C_4$)-alkyl, ($C_1$-$C_4$)-alkoxy, ($C_1$-$C_2$)-alkylenedioxy, F, Cl, $CF_3$ or hydroxyl, phenyl-($C_1$-$C_4$)-alkyl, phenyl-($C_3$-$C_5$)-alkenyl, benzhydryl or benzhydryl-($C_1$-$C_4$)-alkyl, phenyl-($C_1$-$C_4$)-alkanoyl or benzoyl, the phenyl radicals in each case being unsubstituted or substituted by one, two or three radicals from the group comprising methyl, ethyl, methoxy, ethoxy, ($C_1$-$C_2$)-alkylenedioxy, F, Cl, $CF_3$ or hydroxyl, R(9) is phenyl or phenyl-($C_1$-$C_4$)-alkyl, the phenyl radical in each case being unsubstituted or substituted by one, two or three radicals from the group comprising ($C_1$-$C_4$)-alkyl, ($C_1$-$C_4$)-alkoxy, ($C_1$-$C_2$)-alkylenedioxy, F, Cl, $CF_3$ or hydroxyl, R(10) is hydrogen, hydroxyl or methoxy and R(11), R(12), R(13) and R(14) are identical or different and are hydrogen, ($C_1$-$C_8$)-alkyl, ($C_1$-$C_6$)-alkanoyl, phenyl-($C_1$-$C_4$)-alkyl, benzhydryl or benzhydryl-($C_1$-$C_4$)-alkyl, phenyl-($C_1$-$C_4$)-alkanoyl or benzoyl, the phenyl radicals in each case being unsubstituted or substituted by one, two or three radicals from the group comprising methyl, ethyl, methoxy, ethoxy, ($C_1$-$C_2$)-alkylenedioxy, F, Cl, $CF_3$ or hydroxyl.

3. A compound of the formula I as claimed in claim 1, wherein

R(1) is hydrogen, methyl, methoxy, fluorine or chlorine,

R(1)' is hydrogen or methoxy,

R(1)" is hydrogen,

R(2) is hydrogen, methyl, ethyl, propyl, isopropyl, butyl, sec.-butyl, isobutyl, benzyl or phenethyl, R(3) is straight-chain or branched ($C_1$-$C_{12}$)-alkyl, cyclopentyl, cyclohexyl, cyclopentylmethyl, cyclohexylmethyl, allyl, methallyl, benzyl, methylbenzyl, fluorobenzyl, methoxybenzyl, dimethoxybenzyl or phenylethyl, R(4) is hydrogen, methoxy, methyl, chlorine, nitro or hydroxyl, R(4)' is hydrogen, A is the group —$(CH_2)_m$O—$(CH_2)_n$—, m and n each being 2 or 3, or one of the groups —$(CH_2)_p$—CH(OH)—$(CH_2)_q$— and —$(CH_2)_p$—CH(OCH$_2$)—$(CH_2)_q$, p being 1 or 2 and q being 1, or the group —$(CH_2)_r$— O—$CH_2$—CO—, r being 2 or 3, or the group —$(CH_2)_s$—CO—, s being 3 or 4, R(5) is one of the following groups

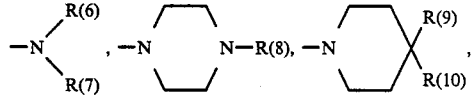

-continued

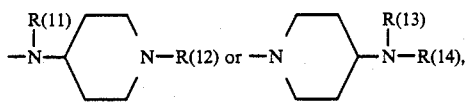

in which
R(6) is hydrogen or methyl,
R(7) is phenyl-(C$_1$-C$_4$)-alkyl, benzhydryl or benzhydryl-(C$_1$-C$_4$)-alkyl, the phenyl radical in each case being unsubstituted or substituted by one, two or three radicals from the group comprising methyl, methoxy, fluorine, chlorine, methylenedioxy or hydroxyl,
R(8) is straight-chain or branched (C$_1$-C$_6$)-alkyl, (C$_1$-C$_6$)-alkanoyl, phenyl, phenyl-(C$_1$-C$_4$)-alkyl, benzhydryl or benzhydryl-(C$_1$-C$_4$)-alkyl, phenyl-(C$_1$-C$_4$)-alkanoyl or benzoyl, the phenyl radicals in each case being unsubstituted or substituted by one, two or three radicals from the group comprising methyl, methoxy, ethoxy, methylenedioxy, fluorine, chlorine or hydroxyl,
R(9) is phenyl, the phenyl radical being unsubstituted or substituted by one, two or three radicals from the group comprising methyl, methoxy, fluorine, chlorine, methylenedioxy or hydroxyl,
R(10) is hydrogen, hydroxyl or methoxy and
R(11), R(12), R(13) and R(14) are identical or different and are hydrogen, (C$_1$-C$_6$)-alkyl, (C$_1$-C$_6$)-alkanoyl, phenyl-(C$_1$-C$_4$)-alkyl, benzhydryl or benzhydryl-(C$_1$-C$_4$)-alkyl, phenyl-(C$_1$-C$_4$)-alkanoyl or benzoyl, the phenyl radials in each case being unsubstituted or substituted by one, two or three radicals from the group comprising methyl, methoxy, methylenedioxy, fluorine, chlorine or hydroxyl.

4. A composition for diminishing the influx of calcium ions into cells which comprises an effective amount of a compound in claim 1 and a pharmaceutically acceptable carrier for the treatment of disturbances in the calcium balance of human or animal in need thereof.

5. Method for the treatment of disturbances of the calcium balance of a human or animal which comprises administersing an effective amount of a compound of the formula I as claimed in claim 1 and a pharmaceutically acceptable carrier.

* * * * *

UNITED STATES PATENT OFFICE
CERTIFICATE OF CORRECTION

PATENT NO. : 4,831,028
DATED : May 16, 1989
INVENTOR(S) : Ulrich Lerch et al

It is certified that error appears in the above-identified patent and that said Letters Patent is hereby corrected as shown below:

ON THE TITLE PAGE

Under [75] Inventors:
Joachim Kaiser of Frankfurt am Main should be listed as the third inventor.

Change "both of Fed. Rep. of Germany" to --all of Fed. Rep. of Germany--.

Claim 3, column 16, line 59, change "2" (1st occurence) to --3--.

Signed and Sealed this

Fifth Day of January, 1993

Attest:

DOUGLAS B. COMER

Attesting Officer     Acting Commissioner of Patents and Trademarks